United States Patent [19]

Rotini et al.

[11] Patent Number: 4,888,178

[45] Date of Patent: Dec. 19, 1989

[54] GALENIC FORMULATIONS WITH PROGRAMMED RELEASE CONTAINING NAPROXEN

[75] Inventors: Leone G. Rotini, Bologna; Egidio Marchi, Casalecchio di Reno, both of Italy

[73] Assignee: Alfa Wassermann S.p.A., Bologna, Italy

[21] Appl. No.: 336,507

[22] Filed: Apr. 12, 1989

Related U.S. Application Data

[63] Continuation of Ser. No. 73,581, Jul. 15, 1987, abandoned.

[30] Foreign Application Priority Data

Jul. 23, 1986 [IT] Italy ................................ 3467 A/86

[51] Int. Cl.⁴ .............................................. A61K 9/24
[52] U.S. Cl. ..................................... 424/468; 424/470; 424/472
[58] Field of Search .................... 424/472, 470, 468

[56] References Cited

U.S. PATENT DOCUMENTS

| | | | |
|---|---|---|---|
| 2,793,979 | 5/1957 | Svedres | 424/470 |
| 3,044,938 | 7/1962 | Halley | 424/470 |
| 4,012,498 | 3/1977 | Kornblum et al. | 424/470 |
| 4,167,588 | 9/1979 | Sheth et al. | 424/465 |
| 4,572,833 | 2/1986 | Pedersen et al. | 424/470 |
| 4,720,387 | 1/1988 | Sakamoto et al. | 424/472 |

*Primary Examiner*—William R. Dixon, Jr.
*Assistant Examiner*—Miriam Sohn
*Attorney, Agent, or Firm*—Birch, Stewart, Kolasch & Birch

[57] ABSTRACT

A galenic formulations are disclosed with programmed release, to be administered orally containing as the active ingredient a compound having antiphlogistic, analgesic and antipyretic activity like, for instance, an arylacetic or an arylpropionic acid, and pharmaceutically acceptable salts thereof. In these new formulations, a portion of the active ingredient is released in a short time, so that the drug can quickly develop its therapeutic action and reach the necessary hematic levels, while the remaining portion of the active constituent is released in a longer interval of time so as to allow therapeutic coverage until subsequent administration. The therapeutic coverage can even last twenty-four hours. Thus, the new galenic formulations object of the present invention are suitable for administration one a day.

15 Claims, No Drawings

GALENIC FORMULATIONS WITH PROGRAMMED RELEASE CONTAINING NAPROXEN

This application is a continuation of application Ser. No. 073,581 filed on July 15, 1987, now abandoned.

BACKGROUND OF THE INVENTION

One of ordinary skill in the art knows well the problems associated with the repeated administrations of drugs. Apart from the troubles and discomforts, mostly psychological, which the patient can experience when he has to remember to take, that determinate medicine three or four times a day (as it happens, for instance, with paracetamol), it must be borne in mind that, from the point of view of absorption kinetics, repeated administration is responsible for very high hematic levels of the drug which repeatedly occur in the organism of the patient, with a remarkable increase in the possibility of side effects. In the literature many methodologies are described, generically called "retard", by means of which the number of repeated administrations of a drug can be reduced while still keeping unaltered its therapeutic effectiveness in time.

Thus, for instance, slow-release tablets of indomethacin, in which the active principle is coated by a film of a hydrophilous polymer and by a cellulose ether, are disclosed in Japanese laid open application J 58170712, while in Japanese laid open application J 59084821, diclofenac, which is another well known antiphlogistic agent, is mixed with β-cyclodestrin. In German laid open application DE 3001797, indoprofen, a good analgesic and antiinflammatory agent which has the drawback of having a short plasmatic half-life, is microencapsulated in a protective layer of a cellulose ether, thus obtaining a remarkable improvement of its plasmatic half-life. Finally, in European publications EP 0094116, EP 0094117 and EP 0094123, granules are described which have a double coating; the first one is made by polyvinylpyrrolidone and the second one is made by acrylic polymers or by cellulose esters or by fatty or oily substances, which should allow a better release of antiphlogistic drugs either in the stomach and in the intestine.

In all of these galenic formulations, however, the initial release of the active ingredient is gradual and slow, so that the therapeutic effect begins only several hours after the administration. This is an evident drawback, especially in the case of drugs which contemporaneously present anti-inflammatory, analgesic and antipyretic activity, in which often a quick release is needed to obtain a prompt analgesic effect, besides the slow and regular release in order to cure the inflammation.

SUMMARY OF THE INVENTION

New galenic formulations with a programmed release, immediate and delayed, are the object of the present invention. These formulations are administrable orally and contain, as the active principle, an anti-inflammatory analgesic and antipyretic drug such as, for instance, an arylacetic or arylpropionic acid, both as the free acid and as the corresponding pharmaceutically acceptable salt with organic or inorganic base. To remove the drawbacks of the known controlled release formulations, and to obtain an adequate therapeutic response from the beginning, the galenic formulations of the present invention are made by a mixture of a granulate having an immediate release with a granulate having a controlled release, in terms of the active ingredient. In this way, by suitably selecting both the kind and the amount of the agents to be used in the manufacture of the two granulates, and the weight ratio between the two types of granulate, it is possible to obtain pharmaceutical formulations having an immediate therapeutic activity which protracts along 12-24 hours, being therefore suitable for once a day administration. We have found that better therapeutic results are obtained when, in the galenic formulations described in the present invention, the active principle is contained in amounts from about 30% to about 70% in weight of the whole weight of the active principle itself both by the immediate release granulate and in the controlled release granulate.

The arylacetic and arylpropionic acids which can advantageously be used for the purposes of the present invention comprise, among the others, internationally known anti-inflammatory agents like naproxen, ibuprofen, indoprofen, ketoprofen, flurbiprofen, diclofenac, indomethacin, fenoprofen, fentiazac and analogs thereof. A preferred aspect of the present invention comprises galenic formulations as described above wherein the active constituent is an anti-inflammatory agent selected from diclofenac, ibuprofen, naproxen and ketoprofen.

Tablets, capsules, sugar coated tablets and granulates for suspension or for solution in suitable liquid media are the preferred galenic formulations of the invention.

In the preparation of the galenic formulations of the present invention, the immediate release granulate is prepared by dry granulating the active principle with suitable adjuvant agents like binding, disintegrating and lubricating agents and then sifting the granules on a sleeve having meshes of 1 mm.

Polyvinylpyrrolidone, carboxymethylcellulose, microcrystalline cellulose, lactose, saccharose, mannitol, gumarabic, pectin and gelatin can be advantageously used as binding agents.

Starch, sodium starch glycolate, alginates and reticutaled polyvinylpirrolidone can be used as disintegrating agents.

Talc, magnesium stearate, stearic acid and silica gel can be used as lubricating agents.

Polyvinylpyrrolidone, lactose, maize starch, sodium starch glycolate and magnesium stearate are the preferred adjuvants in the present invention.

The granulate having a controlled release, in its turn, is prepared by wet granulating the active principle together with the retarding agents by means of a solvent selected from an alcohol containing from 1 to 4 carbon atoms, an aromatic hydrocarbon, a ketone containing from 3 to 6 carbon atoms, an alkyl halide containing from 1 to 4 carbon atoms, mixtures thereof or mixtures thereof with water, then drying the granules in oven at 50° C. and sifting them through a sieve having meshes of 1 mm.

Alcohols containing from 1 to 4 carbon atoms and their mixtures with water are the preferred solvents, mostly 95% ethyl alcohol.

Many retarding agents can be advantageously used; they are preferably selected among ethylcellulose, methylcellulose, polyvinylacetate, metacrylic acid esters, cellulose acetate, fatty alcohols containing from 12 to 32 carbon atoms, glyceric esters of fatty acids containing from 10 to 22 carbon atoms, like the mono- and di-stearate of glycerile, esters of fatty acids and alcohols having from 12 to 31 carbon atoms, paraffin, natural waxy substances like beeswax, unbleached wax, candelilla wax, carnauba wax, sealing wax, spermaceti, ozokerite and hydrogenated vegetable oils like hydrogenated castor oil, hydrogenated peanut oil, hydrogenated cotton seed oil and mixtures thereof.

Methylcellulose, ethylcellulose, hydrogenated vegetable oils and mixtures thereof are the retarding agents preferred in the present invention.

The two granulates are mixed in such weight ratios that the active principle contained in the final galenic formulation belongs to each one of the two granulates for a percent comprised between about 30% and about 70% of the whole active principle.

The granulate having immediate release contains from about 60% to about 70% of active principle, from about 20% to about 30% of binding agents, from about 8% to about 12% of disintegrating agents and from about 0.2% to about 1% of a lubricating agent.

The granulate having controlled release contains from about 60% to about 70% of active principle and from about 30% to about 40% of a retarding agent or of a mixture of retarding agents.

In a preferred, but not limiting, aspect of the invention, when naproxen is the antiphlogistic drug used as active principle, the composition of the granulates is as follows:

(a) Granulate having immediate release:
from 60% to 70% of naproxen, from 17% to 23% of lactose, from 3% to 7% of polyvinylpyrrolidone, from 4% to 8% of maize starch, from 3% to 6% of sodium starch glycolate, from 0.2% to 0.5% of magnesium stearate.

(b) Granulate having controlled release:
from 60% to 70% of naproxen, from 20% to 30% of hydrogenated castor oil, from 6% to 12% of ethylcellulose.

The two granulates are mixed in such weight ratios that the percents of naproxen present in the two granulates of the final galenic formulation are comprised between 30% and 70% of the whole amount of naproxen present in the formulation itself.

Some examples of galenic formulations obtained according to that previously mentioned are hereunder reported in order to illustrate the invention; nevertheless such examples are not to be interpreted as a limitation of the invention itself.

EXAMPLE 1

| Tablet containing 750 mg of naproxen | |
| --- | --- |
| Composition of the granulate having immediate release in mg/tablet | |
| naproxen | 300 |
| lactose | 88.8 |
| polyvinylpyrrolidone | 18 |
| maize starch | 30 |
| sodium starch glycolate | 18 |
| magnesium stearate | 1.2 |
| Composition of the granulate having controlled release in mg/tablet | |
| naproxen | 450 |
| hydrogenated castor oil | 171 |
| ethylcellulose | 54 |

EXAMPLE 2

| Tablet containing 500 mg of naproxen | |
| --- | --- |
| Composition of the granulate having immediate release in mg/tablet | |
| naproxen | 300 |
| lactose | 88.8 |
| polyvinylpyrrolidone | 18 |
| maize starch | 30 |
| sodium starch glycolate | 18 |
| magnesium stearate | 1.2 |
| Composition of the granulate having controlled release in mg/tablet | |
| naproxen | 200 |
| hydrogenated castor oil | 76 |
| ethylcellulose | 24 |

EXAMPLE 3

| Granular for solution or suspension containing 500 mg of naproxen | |
| --- | --- |
| Composition in mg of the granulate having immediate release | |
| naproxen | 250 |
| lactose | 74 |
| polyvinylpyrrolidone | 15 |
| maize starch | 25 |
| sodium starch glycolate | 15 |
| magnesium stearate | 1 |
| Composition in mg of the granulate having controlled release | |
| naproxen | 250 |
| hydrogenated castor oil | 95 |
| ethylcellulose | 30 |
| orange granular | 2000 |

EXAMPLE 4

| Capsule containing 375 mg of naproxen | |
| --- | --- |
| Composition of the granulate having immediate release in mg/capsule | |
| naproxen | 175 |
| lactose | 55.4 |
| polyvinylpyrrolidone | 11.2 |
| maize starch | 18.7 |
| sodium starch glycolate | 11.2 |
| magnesium stearate | 0.8 |
| Composition of the granulate having controlled release in mg/capsule | |
| naproxen | 200 |
| hydrogenated castor oil | 76 |
| ethylcellulose | 24 |

Pharmacokinetic tests have been carried out in man to verify the effectiveness, both immediate and long term of the above described galenic formulations.

These pharmacokinetic tests have been carried out on groups each made of six healthy volunteers, by examining the hematic levels of naproxen 2, 3, 4, 6, 8, 10, 12, 24 and 36 hours after the administration of the galenic formulations.

The values reported in the following Table 1 are calculated over the mean of the values of the single values of the six healthy volunteers; the naproxen has been checked in the plasma by spectrophotometric route at 272 nm after crossing through a column for liquid chromatography under high pressure (HPLC) by the using a LC 601 Perkin-Elmer apparatus; the values are expressed in mcg/ml of plasma.

TABLE 1

| Times of drawing hours | Example 1 (mcg/ml) | Example 2 (mcg/ml) | Example 3 (mcg/ml) | Example 4 (mcg/ml) |
|---|---|---|---|---|
| Hematic levels of naproxen expressed in mcg/ml of human plasma | | | | |
| 2 | 35.7 | 43.9 | 57.0 | 39.4 |
| 3 | 42.8 | 48.3 | 52.2 | 41.1 |
| 4 | 44.3 | 45.7 | 48.6 | 40.8 |
| 6 | 50.1 | 54.8 | 57.8 | 46.5 |
| 8 | 48.4 | 47.9 | 51.8 | 40.9 |
| 10 | 49.6 | 45.3 | 46.9 | 38.1 |
| 12 | 52.8 | 34.5 | 39.8 | 34.3 |
| 24 | 38.1 | 20.6 | 26.2 | 17.1 |
| 32 | 30.9 | 15.8 | 19.0 | 13.7 |

We claim:

1. A galenic formulation for oral administration having a programmed release and containing naproxen as an active ingredient, which is formed by a mixture comprising:
   (a) a granulate having immediate release including from about 30% to about 70% by weight of the total amount of naproxen in said formulation in admixture with a binding agent, a disintegrating agent, and a lubricating agent; and
   (b) a granulate having a controlled release including from about 30% to about 70% by weight of the total amount of naproxen in said formulation in admixture with hydrogenated castor oil and ethylcellulose as retarding agents.

2. The galenic formulation of claim 1, which is in the form of a tablet, a capsule, a sugard coated tablet or a granulate for suspension or for solution in suitable liquid media.

3. The galenic formulation of claim 1, wherein said binding agent is a member selected from the group consisting of polyvinylpyrrolidone, carboxymethylcellulose, microcrystalline cellulose, lactose, saccharose, mannitol, gumarabic, pectin, and gelatin.

4. The galenic formulation of claim 1, wherein said disintegrating agent is a member selected from the group consisting of starch, sodium starch glycolate, alginates, and reticutaled polyvinylpirrolidone.

5. The galenic formulation of claim 1, wherein said lubricating agent is a member selected from the group consisting of talc, magnesium stearate, stearic acid, and silica gel.

6. A galenic formulation for oral administration having a programmed release and containing naproxen as an active ingredient, which is formed by a mixture comprising:
   (a) a granulate having immediate release including from about 30% to about 70% by weight of the total amount of naproxen in said formulation in admixture with a binding agent, a disintegrating agent, and a lubricating agent, wherein said immediate release granulate is composed of about 60% to about 70% by weight of naproxen, about 20% to about 30% by weight of a binding agent; about 8% to about 12% by weight of a disintegrating agent, and about 0.2% to about 1% by weight of a lubricating agent; and
   (b) a granulate having a controlled release including from about 30% to about 70% by weight of the total amount of naproxen in said formulation in admixture with hydrogenated castor oil and ethylcellulose as retarding agents, wherein said controlled release granulate is composed of about 60% to about 70% by weight of naproxen and about 30% to about 40% by weight of said retarding agents.

7. The galenic formulation of claim 6, which is in the form of a tablet, a capsule, a sugar coated tablet or a granulate for suspension or for solution in suitable liquid media.

8. The galenic formulation of claim 6, wherein said binding agent is a member selected from the group consisting of polyvinylpyrrolidone, carboxymethylcellulose, microcrystalline cellulose, lactose, saccharose, mannitol, gumarabic, pectin, and gelatin.

9. The galenic formulation of claim 6, wherein said disintegrating agent is a member selected from the group consisting of starch, sodium starch glycolate, alginates, and reticulated polyvinylpirrolidone.

10. The galenic formulation of claim 6, wherein said lubricating agent is a member selected from the group consisting of talc, magnesium stearate, stearic acid, and silica gel.

11. The galenic formulation of claim 6, wherein said granulate (a) is composed of 60% to 70% by weight of naproxen, 17% to 23% by weight of lactose, 3% to 7% by weight of polyvinylpyrrolidone, 4% to 8% by weight of maize starch, 3% to 6% by weight of sodium starch glycolate, and 0.2% to 0.5% by weight of magnesium stearate; and said granulate (b) is composed of 60% to 70% by weight of naproxen, 20% to 30% by weight of hydrogenated castor oil, and 6% to 12% by weight of ethylcellulose.

12. The galenic formulation of claim 6, which is in the form of a tablet containing 750 mg of naproxen, wherein the composition of granulate (a) is the following:

| component | mg |
|---|---|
| naproxen | 300 |
| lactose | 88.8 |
| polyvinylpyrrolidone | 18 |
| maize starch | 30 |
| sodium starch glycolate | 18 |
| magnesium stearate | 1.2 | and the composition of granulate (b) is the following:

| component | mg |
|---|---|
| naproxen | 450 |
| hydrogenated castor oil | 171 |
| ethylcellulose | 54 |

13. The galenic formulation of claim 6, which is in the form of a tablet containing 500 mg of naproxen, wherein the composition of granulate (a) is the following:

| component | mg |
|---|---|
| naproxen | 300 |
| lactose | 88.8 |
| polyvinylpyrrolidone | 18 |
| maize starch | 30 |
| sodium starch glycolate | 18 |
| magnesium stearate | 1.2 | and the composition of granulate (b) is the following:

| component | mg |
|---|---|
| naproxen | 200 |
| hydrogenated castor oil | 76 |

| component | mg |
|---|---|
| ethylcellulose | 24 |

14. The galenic formulation of claim 6, which is in the form of a granular for solution or suspension containing 500 mg of naproxen, wherein the composition of granulate (a) is the following:

| component | mg |
|---|---|
| naproxen | 250 |
| lactose | 74 |
| polyvinylpyrrolidone | 15 |
| maize starch | 25 |
| sodium starch glycolate | 15 |
| magnesium stearate | 1 | and the composition of granulate (b) is the following:

| component | mg |
|---|---|
| naproxen | 250 |
| hydrogenated castor oil | 95 |

| component | mg |
|---|---|
| ethylcellulose | 30 | and said formulation contains 2000 mg of orange granular.

15. The galenic formulation of claim 6, which is in the form of a capsule containing 375 mg of naproxen, wherein the composition of granulate (a) is the following:

| component | mg |
|---|---|
| naproxen | 175 |
| lactose | 55.4 |
| polyvinylpyrrolidone | 11.2 |
| maize starch | 18.7 |
| sodium starch glycolate | 11.2 |
| magnesium stearate | 0.8 | and the composition of granulate (b) is the following:

| component | mg |
|---|---|
| naproxen | 200 |
| hydrogenated castor oil | 76 |
| ethylcellulose | 24 |

* * * * *